United States Patent
Takeshita

(10) Patent No.: US 8,994,360 B2
(45) Date of Patent: Mar. 31, 2015

(54) MICROORGANISM NUMBER MEASUREMENT DEVICE

(75) Inventor: Toshiaki Takeshita, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 255 days.

(21) Appl. No.: 13/580,781

(22) PCT Filed: Nov. 9, 2011

(86) PCT No.: PCT/JP2011/006250
§ 371 (c)(1),
(2), (4) Date: Aug. 23, 2012

(87) PCT Pub. No.: WO2012/066747
PCT Pub. Date: May 24, 2012

(65) Prior Publication Data
US 2013/0229168 A1 Sep. 5, 2013

(30) Foreign Application Priority Data
Nov. 17, 2010 (JP) ................. 2010-256561

(51) Int. Cl.
*G01N 27/00* (2006.01)
*G01N 15/10* (2006.01)
(Continued)

(52) U.S. Cl.
CPC .......... *G01N 15/1031* (2013.01); *G01N 27/447* (2013.01); *C12Q 1/18* (2013.01); *G01N 15/0656* (2013.01); *C12M 41/36* (2013.01)
USPC ...................... 324/71.4; 324/76.16

(58) Field of Classification Search
CPC ... C12Q 1/18; G01N 15/0656; G01N 27/447; G01N 15/1031; C12M 41/36
USPC ........ 324/71.4, 691, 439, 722, 600, 633, 638, 324/637, 639, 158.1, 692, 76.16, 76.39, 324/76.48, 76.62; 422/68.1, 73, 82.01; 436/150, 69, 523, 10; 73/861.41
See application file for complete search history.

(56) References Cited

U.S. PATENT DOCUMENTS 3,971,703 A 7/1976 Picciolo et al.
4,433,299 A * 2/1984 Kawai et al. ................... 204/549
(Continued)

FOREIGN PATENT DOCUMENTS

JP 56-66748 A 6/1981
JP 56066748 * 6/1981 ............. G01N 27/30
(Continued)

OTHER PUBLICATIONS
JP 56-066748 English Translation.*
(Continued)

*Primary Examiner* — Huy Q Phan
*Assistant Examiner* — Raul Rios Russo
(74) *Attorney, Agent, or Firm* — RatnerPrestia

(57) ABSTRACT

A microorganism number-measuring apparatus includes: a container holder for holding container having an opening in the upper surface of the container, with the opening being positioned upward; and a rotary driver for rotating a liquid accommodated in container held by the holder, about the rotary axis in the up-and-down direction. Moreover, the apparatus includes: an electrode inserting part for inserting measurement chip to a position from above container held by the holder, via the opening, with the position being closer to the container's inner surface than to the container's center axis and being away from the container's inner surface with a predetermined distance; and a measurement unit for measuring microorganisms using measurement electrode of measurement chip inserted into container by the electrode inserting part. The electrode inserting part holds measurement chip, in a state of measurement electrode facing the container's inner-surface.

6 Claims, 25 Drawing Sheets

(51) Int. Cl.
  *C12Q 1/18* (2006.01)
  *G01N 15/06* (2006.01)
  *C12M 1/34* (2006.01)
  *G06M 1/10* (2006.01)
  *G01N 27/447* (2006.01)

(56) References Cited

U.S. PATENT DOCUMENTS

| | | |
|---|---|---|
| 6,002,789 A | 12/1999 | Olsztyn et al. |
| 2003/0098690 A1* | 5/2003 | Higo .............................. 324/439 |
| 2007/0207538 A1* | 9/2007 | Amano ...................... 435/289.1 |
| 2008/0153153 A1* | 6/2008 | Takenaka et al. .......... 435/287.5 |
| 2009/0188328 A1* | 7/2009 | Iijima ........................ 73/861.12 |
| 2009/0223824 A1 | 9/2009 | Oouchi |
| 2010/0060367 A1* | 3/2010 | Harima et al. .................. 331/68 |
| 2010/0117745 A1* | 5/2010 | Moriya ........................... 331/68 |
| 2010/0193358 A1 | 8/2010 | Hamada |

FOREIGN PATENT DOCUMENTS

| | | |
|---|---|---|
| JP | 2002-330752 A | 11/2002 |
| JP | 2009-207431 A | 9/2010 |
| JP | 2010-187626 A | 9/2010 |
| JP | 2010-220507 A | 10/2010 |
| JP | 2010-223657 A | 10/2010 |
| JP | 2012-544096 | 2/2015 |
| WO | WO 2009/037804 A1 | 3/2009 |

OTHER PUBLICATIONS

JP International Search Report for PCT/JP2011/006250, Feb. 14, 2012.

* cited by examiner

US 8,994,360 B2

MICROORGANISM NUMBER MEASUREMENT DEVICE

This application is a U.S. National Phase Application of PCT International Application PCT/JP2011/006250, filed Nov. 9, 2011.

TECHNICAL FIELD

The present invention relates to a microorganism number-measuring apparatus, in particular to a microorganism number-measuring apparatus for measuring the number of microorganisms present in an oral cavity or the like.

BACKGROUND ART

A method for measuring the number of microorganisms by using a conventional microorganism number-measuring apparatus is described.

First, a user collects the microorganisms from the inside of an oral cavity through the use of a microorganism sampling tool such as a cotton swab. Next, the user immerses the microorganism sampling tool into a liquid in a container via an upper surface opening of the container. After that, the microorganism number-measuring apparatus agitates the liquid in the container with an agitator, and measures the number of the microorganisms with a measurement electrode disposed in the container, in a state where the liquid is being agitated (see Patent Literature 1, for example).

In such the conventional microorganism number-measuring apparatus, the size of the apparatus itself can be made considerably small because it is possible to both release and measure the microorganisms in the inside of the container.

However, the container for use in the measurement has to be such that the container's inner wall surface and the measurement electrode are integrally made. Moreover, extraction wires from the measurement electrode to the outside of the container are required to be made watertight for avoiding a liquid leakage, resulting in a high cost of manufacturing.

Therefore, use of the conventional microorganism number-measuring apparatus for measuring the number of microorganisms results in a high cost of measurement.

CITATION LIST

Patent Literature

Patent Literature 1: Japanese Patent Unexamined Publication No. 2010-220507

SUMMARY OF THE INVENTION

In view of the aforementioned problems, the present invention is made to provide a microorganism number-measuring apparatus that allows a reduction in measurement costs and an increase in measurement accuracy.

The invention is intended to provide the microorganism number-measuring apparatus that includes: a container holder that holds a container having an opening in the upper surface thereof, with the opening being positioned upward; and a rotary driver that rotates a liquid about a rotary axis in the up-and-down direction, with the liquid being accommodated in the container held by the container holder. Moreover, the apparatus includes: an electrode inserting part that inserts a measurement chip from above the container held by the container holder, via the opening, to a position in the container, with the position being closer to the container's inner surface than to the container's center axis and being away from the container's inner surface with a predetermined distance; and a measurement unit that measures microorganisms by using a measurement electrode of the measurement chip inserted into the container by the electrode inserting part. In addition, the electrode inserting part holds the measurement chip, with the measurement electrode facing the container's inner surface.

DESCRIPTION OF EMBODIMENTS

Hereinafter, detailed descriptions of an embodiment according to the present invention will be made, with reference to the drawings.

Figure 1:
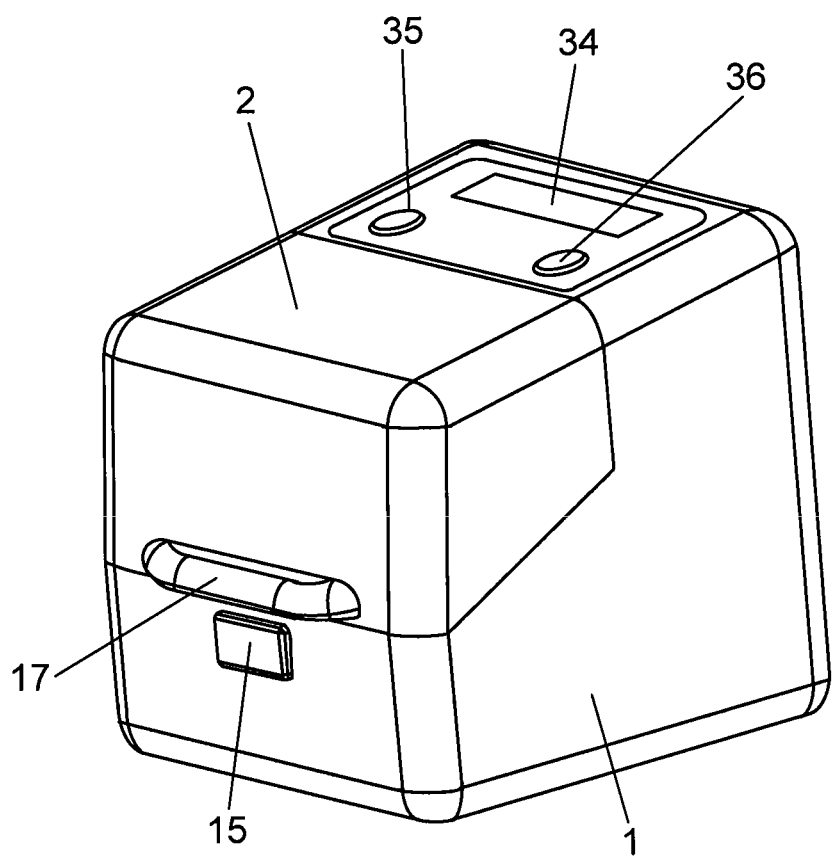
FIG. 1 is a perspective view of a microorganism number-measuring apparatus according to an embodiment of the present invention.
Figure 2:
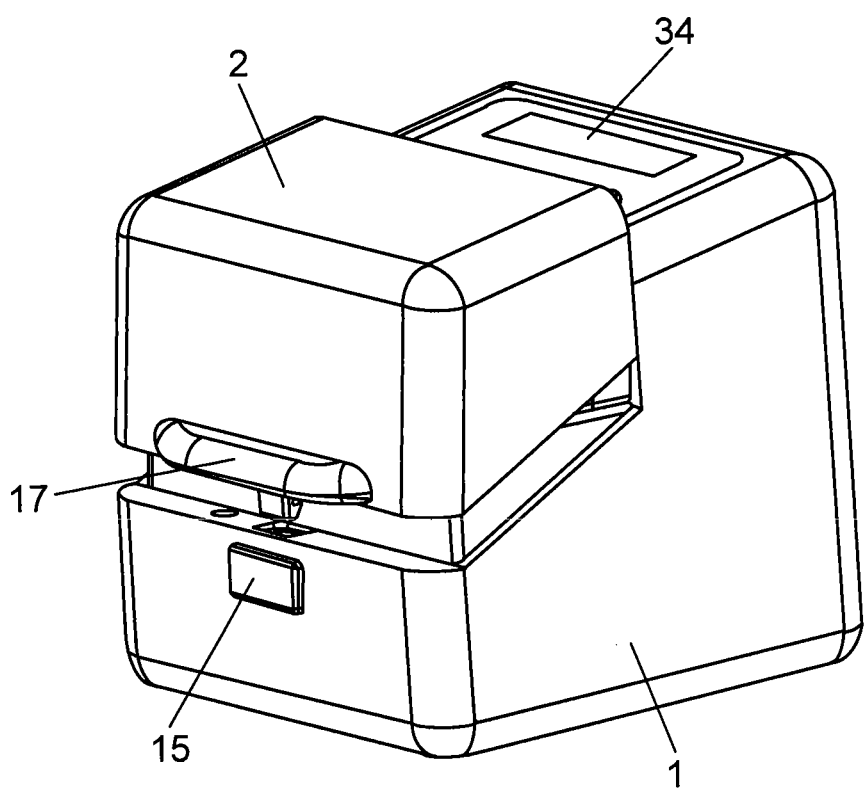
FIG. 2 is a perspective view of the microorganism number-measuring apparatus in operation according to the embodiment of the invention.
Figure 3:
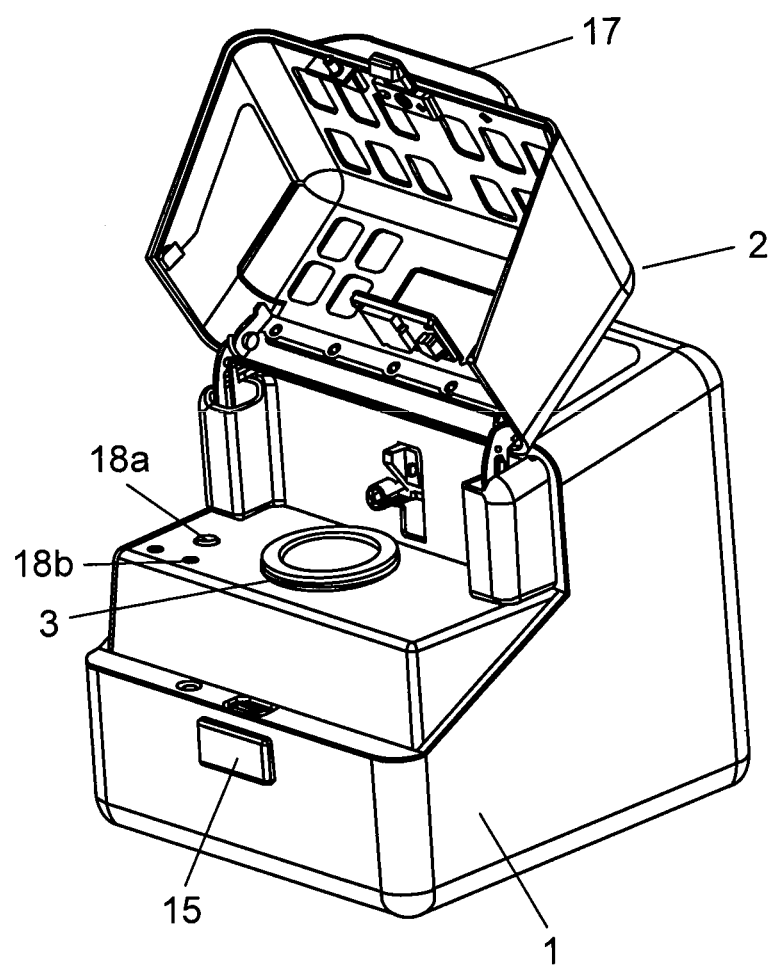
FIG. 3 is a perspective view of the microorganism number-measuring apparatus in operation according to the embodiment of the invention.
Figure 4:
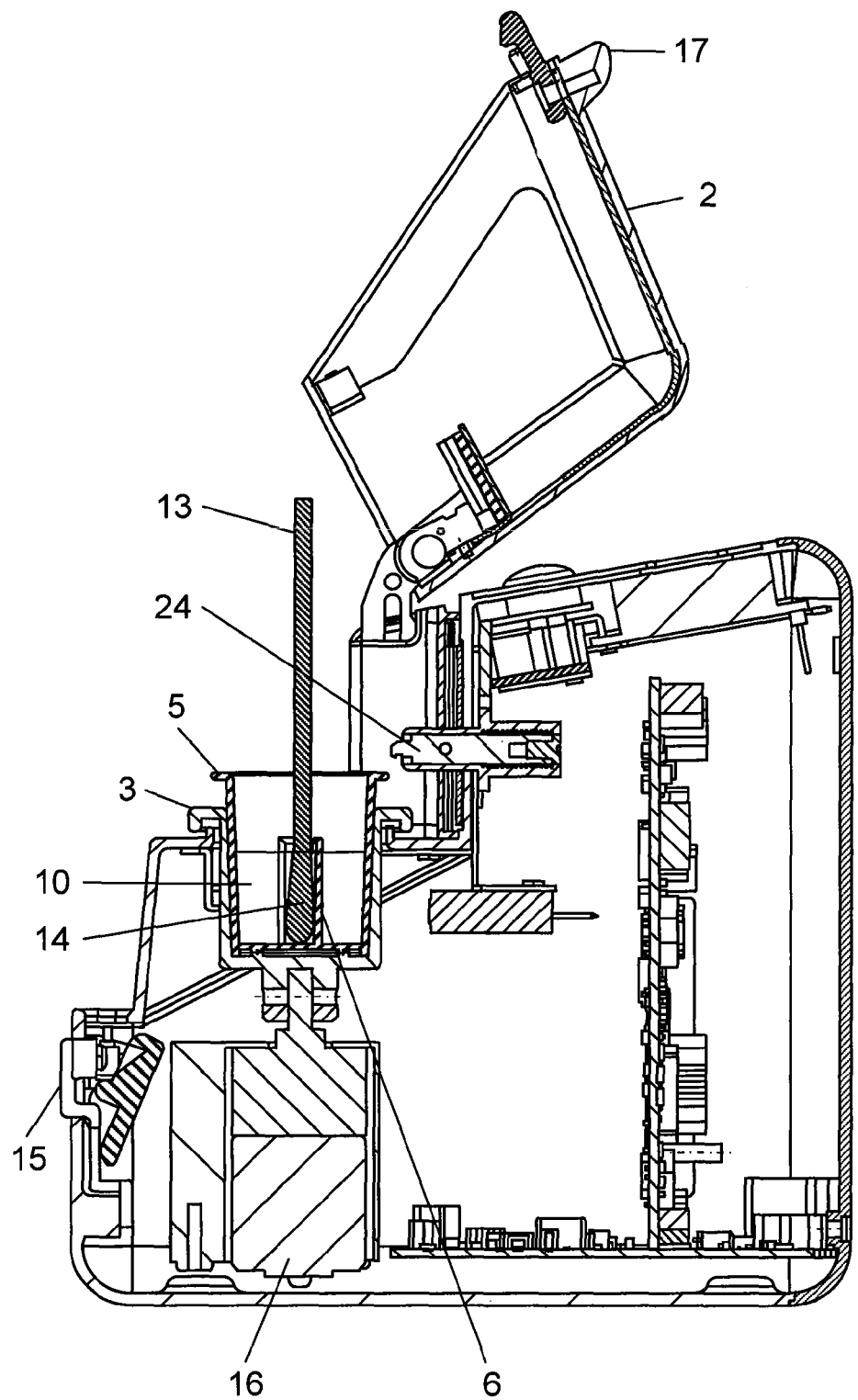
FIG. 4 is a cross-sectional view of the microorganism number-measuring apparatus in operation according to the embodiment of the invention.
Figure 5:
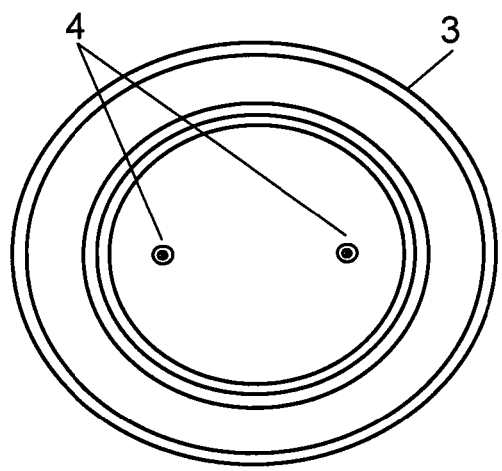
FIG. 5 is a plan view of a vicinity of a container holder of the microorganism number-measuring apparatus according to the embodiment of the invention.

FIG. 1 is a perspective view of microorganism number-measuring apparatus 100 according to the embodiment of the present invention. FIG. 2 is a perspective view of microorganism number-measuring apparatus 100 in operation. FIG. 3 is another perspective view of microorganism number-measuring apparatus 100 in operation. FIG. 4 is a cross-sectional view of microorganism number-measuring apparatus 100 in operation. FIG. 5 is a plan view of a vicinity of container holder 3 of microorganism number-measuring apparatus 100.

Microorganism number-measuring apparatus 100 includes box-shaped body case 1. In body case 1, front cover 2 is disposed in an openable and closeable manner, as shown in FIGS. 1 to 3. Details of the open/close structure of front cover 2 will be described later.

When front cover 2 is opened, front cover 2 is first lifted upward as shown in from FIG. 1 to FIG. 2, and then front cover 2 is moved rotationally upward from the state shown in FIG. 2 to one in FIG. 3.

As shown in FIG. 3, container holder 3 is disposed at a part in body case 1, with the part being exposed to the outside when front cover 2 is opened. Container holder 3 is one that has a blind-cylinder shape, the upper surface of which is open, as shown in FIGS. 3 and 4. On the inner surface of the bottom of container holder 3, drive projections 4 are disposed which protrude in the direction toward the container and face each other through an angle of 180 degrees, as shown in FIG. 5. Note that container holder 3 holds an outer peripheral surface of the blind-cylinder-shaped container 5 having an opening in the upper surface thereof, and a bottom part of the container, as shown in FIG. 4.

Figure 6:
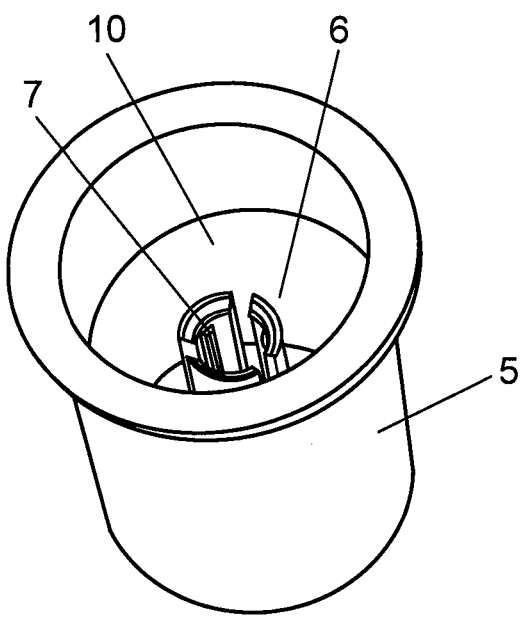
FIG. 6 is a perspective view of a container of the microorganism number-measuring apparatus according to the embodiment of the invention.
Figure 7A:
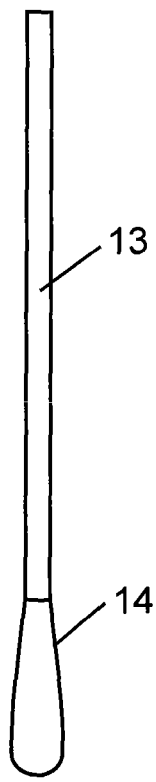
FIG. 7A is a side-elevational view showing a configuration of a microorganism sampling tool for use in the microorganism number-measuring apparatus according to the embodiment of the invention.
Figure 7B:
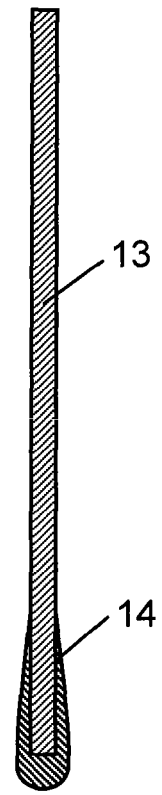
FIG. 7B is a cross-sectional view showing the configuration of the microorganism sampling tool for use in the microorganism number-measuring apparatus according to the embodiment of the invention.
Figure 7C:
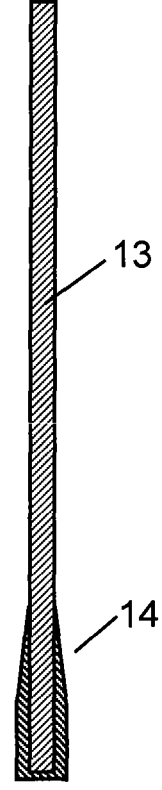
FIG. 7C is a cross-sectional view showing the configuration of the microorganism sampling tool for use in the microorganism number-measuring apparatus according to the embodiment of the invention.
Figure 8A:
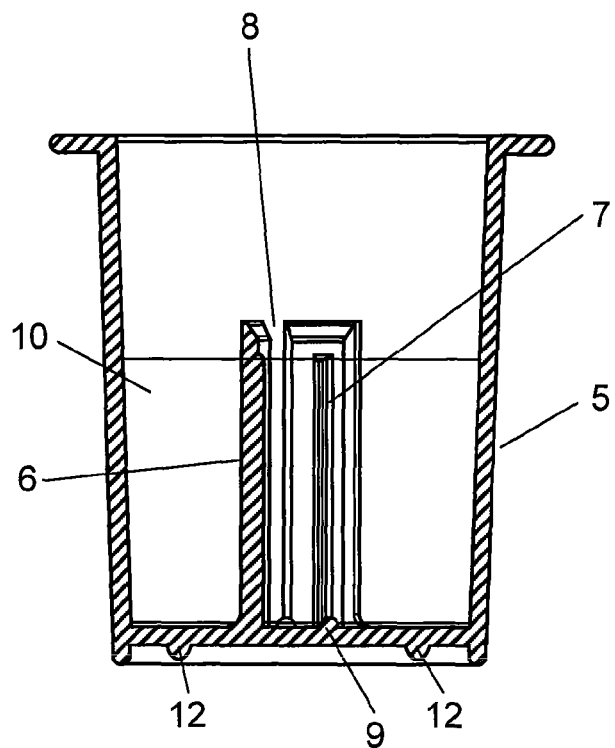
FIG. 8A is a cross-sectional view of the container of the microorganism number-measuring apparatus according to the embodiment of the invention.
Figure 8B:
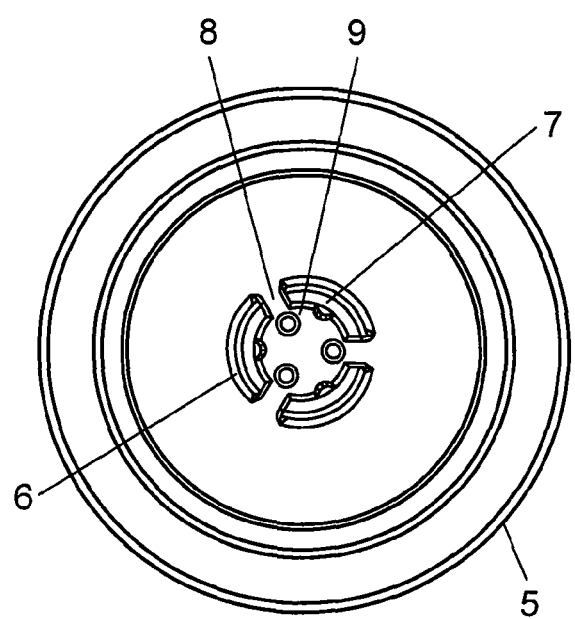
FIG. 8B is a plan view of the container of the microorganism number-measuring apparatus according to the embodiment of the invention.
Figure 9:
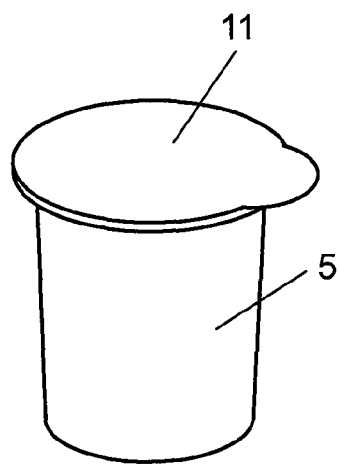
FIG. 9 is a perspective view, as viewed from above, of the container of the microorganism number-measuring apparatus according to the embodiment of the invention.
Figure 10:
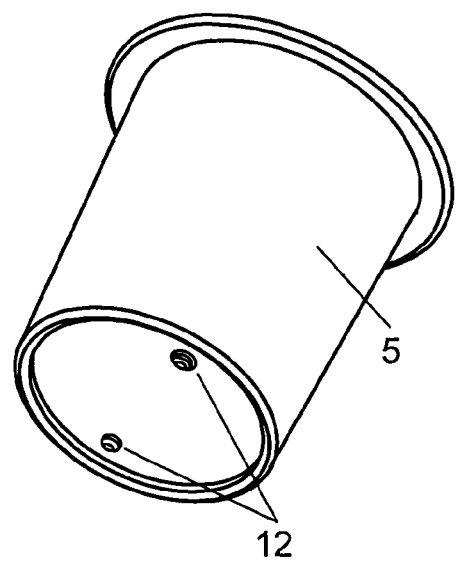
FIG. 10 is a perspective view, as viewed from below, of the container of the microorganism number-measuring apparatus according to the embodiment of the invention.

FIG. 6 is a perspective view of container 5 of microorganism number-measuring apparatus 100 according to the embodiment of the invention. FIGS. 7A to 7C are views that each show a configuration of microorganism sampling tool 13 for use in microorganism number-measuring apparatus 100. Incidentally, FIG. 7A is a side-elevational view, and FIGS. 7B and 7C are each a cross-sectional view. FIG. 8A is a cross-sectional view of container 5 of microorganism number-measuring apparatus 100. FIG. 8B is a plan view of container 5 of microorganism number-measuring apparatus 100. FIG. 9 is a perspective view, as viewed from above, of container 5 of microorganism number-measuring apparatus 100. FIG. 10 is a perspective view, as viewed from below, of container 5 of microorganism number-measuring apparatus 100.

As shown in FIGS. 6, 8A, and 8B, holding body 6 having a cylinder shape is formed on the inner surface of the bottom of container 5. On the inner side surface of holding body 6, three of release projections 7 which each extend in the up-and-down direction are formed at 120 degrees intervals.

Moreover, in holding body 6, three of release slots 8 are formed at 120 degrees intervals, with the slots each penetrating the body from the inside to the outside thereof. In addition, three of release projections 9 are formed at the bottom of holding body 6, at 120 degrees intervals, between the separated-by-slot parts of the holding body.

Note that, in container 5, pure water 10 is accommodated as a liquid into which microorganisms are released. In addition, lid 11 is set on the opening in the upper surface of the container for preventing pure water 10 from spilling when transporting the container (see FIG. 9).

Moreover, as shown in FIGS. 8A and 10, projections 12 are disposed to face each other through an angle of 180 degrees on the outer surface of the bottom of container 5, with the projections engaging with drive projections 4 of container holder 3.

Holding body 6 of container 5 is intended to insert therein, from above, sampling portion 14 that is disposed at the lower end of stick-like microorganism sampling tool 13 shown in FIGS. 7A to 7C. Releasing of the microorganisms into pure water 10 is performed in a state where the sampling portion is inserted. That is, a user releases the microorganisms into pure water 10, with the microorganisms having been collected with sampling portion 14 of microorganism sampling tool 13, by inserting sampling portion 14 into the inside of an oral cavity.

Hereinafter, descriptions of the releasing of the microorganisms into pure water 10 will be made.

First, the user pushes operation button 15 disposed on a lower part of the front of body case 1. This causes front cover 2 to be unlocked, and front cover 2 is lifted slightly upward.

Figure 11:
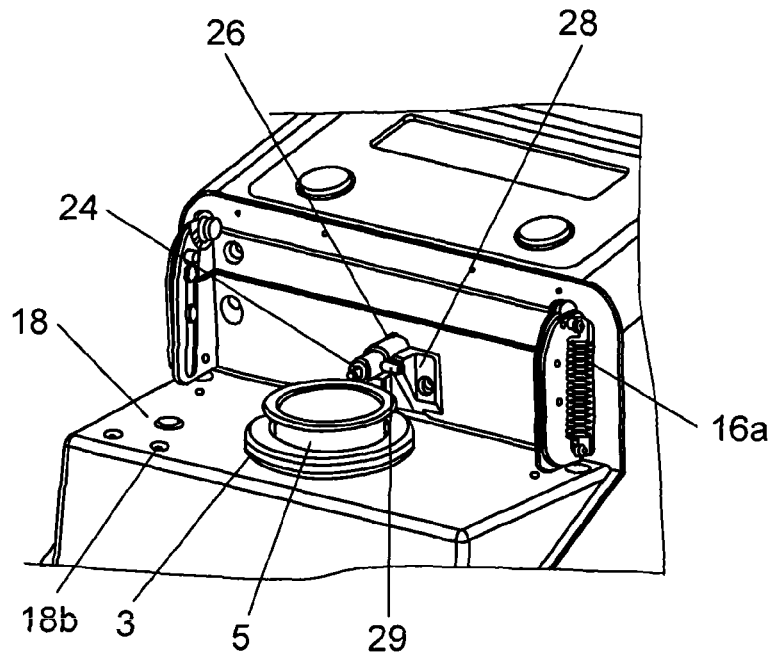
FIG. 11 is a partial perspective view of a vicinity of the container holder, with a front cover being closed, in the microorganism number-measuring apparatus according to the embodiment of the invention.
Figure 12:
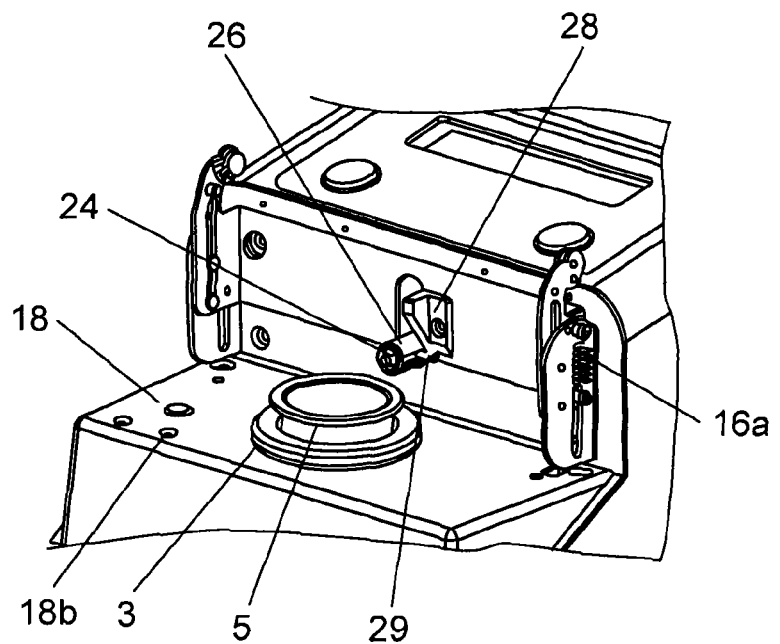
FIG. 12 is a partial perspective view of the vicinity of the container holder, with the front cover being opened, in the microorganism number-measuring apparatus according to the embodiment of the invention.

FIG. 11 is a partial perspective view of a vicinity of container holder 3, with front cover 2 being closed, in microorganism number-measuring apparatus 100 according to the embodiment of the invention. FIG. 12 is a partial perspective view of the vicinity of the container holder, with front cover 2 being opened, in microorganism number-measuring apparatus 100.

In order to lift front cover 2 upward, springs 16a as shown in FIG. 11 are set in the both sides of the inside of front cover 2. As described above, when front cover 2 is unlocked, fully-stretched springs 16a return from the state shown in FIG. 11 to their original one shown in FIG. 12. By their return force, front cover 2 is lifted upward. Incidentally, in FIGS. 11 and 12, front cover 2 and the like are omitted for easy understanding of such as the operation of lifting front cover 2.

Then, starting with the state (the state shown in FIG. 2) where front cover 2 is lifted upward in this way, the user grips handle 17 disposed in the lower end of the front of front cover 2, and lifts and opens front cover 2 such that container holder 3 is exposed from body case 1, as shown in FIG. 3.

Figure 13:
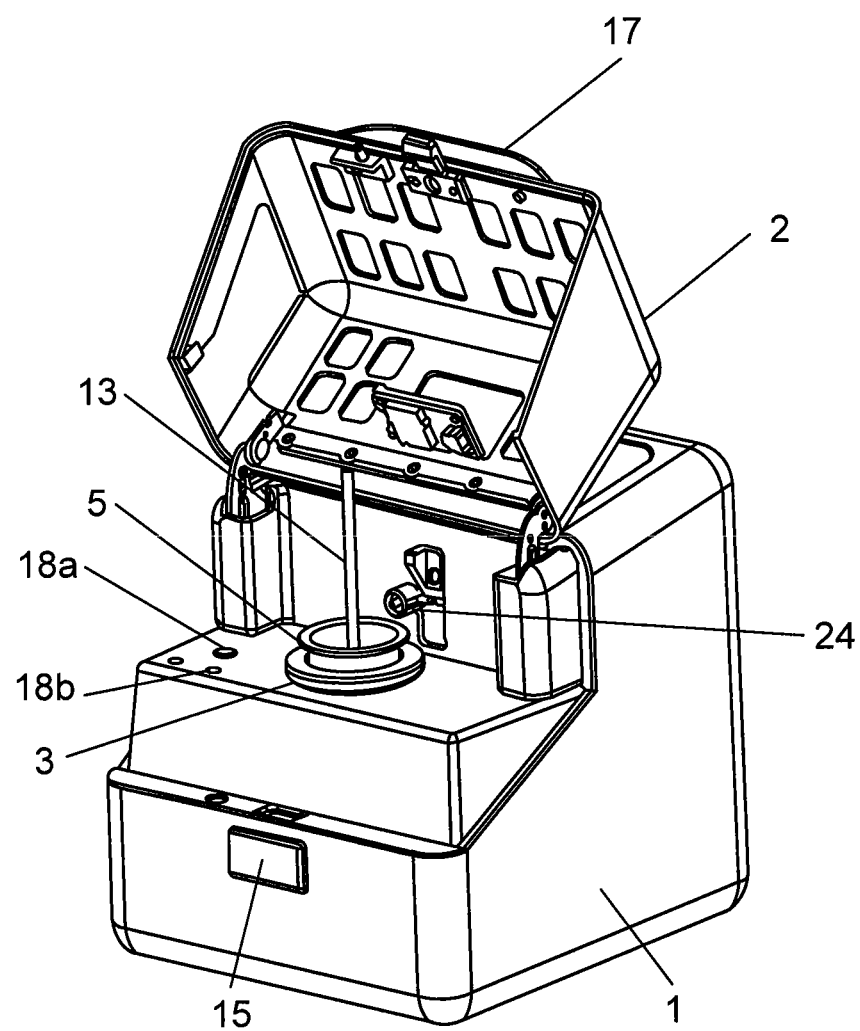
FIG. 13 is a perspective view showing a state where the container is set, in the microorganism number-measuring apparatus according to the embodiment of the invention.

FIG. 13 is a perspective view showing a state where container 5 is set, in microorganism number-measuring apparatus 100 according to the embodiment of the invention.

As shown in FIG. 9, lid 11 is set on the opening in the upper surface of container 5. Therefore, the user inserts a lower part of container 5 from an opening in the upper surface of container holder 3 as shown in FIGS. 4 and 13, with lid 11 having been removed from the opening in the upper surface of container 5. With this operation, the lower part and the outer peripheral part of container 5 are held by container holder 3.

In container 5 held by container holder 3, pure water 10 is accommodated as shown in FIG. 8A. Then, the user inserts, into pure water 10, sampling portion 14 of microorganism sampling tool 13 shown in FIGS. 7A to 7C. Prior to this, the user inserts, into the oral cavity, sampling portion 14 of microorganism sampling tool 13 that is in the state (unused state) shown in FIGS. 7A and 7B, and collects the microorganisms present in the oral cavity by means of sampling portion 14.

The user inserts sampling portion 14 of microorganism sampling tool 13 from above holding body 6 as shown in FIG. 4. At this time, front cover 2 has been rotationally moved to a rearward position of a space above the opening in the upper surface of container 5, as shown in FIGS. 4 and 13. With this configuration, it is possible to remarkably-simply perform the operation of inserting sampling portion 14 of microorganism sampling tool 13 into holding body 6.

On the outer surface of the bottom of container 5, projections 12 are disposed as shown in FIGS. 8A and 10. Moreover, on the inner surface of the bottom of container holder 3 that holds container 5, drive projections 4 are disposed as shown in FIG. 5.

Accordingly, with drive projections 4 engaging with projections 12, the rotation of container holder 3 by motor 16 (FIG. 4) results in the rotation of container 5 as well.

Note that, for starting the rotation of motor 16, switch 18a shown in FIG. 3 is pushed. When pushing switch 18a, for example, the user pushes switch 18a with the user's left hand, while the user is holding an upper part of microorganism sampling tool 13 shown in FIGS. 4 and 13 with the user's right hand.

In this example, being held by the right hand, microorganism sampling tool 13 is kept in a stationary state without rotation. On the other hand, as described above, container 5 is rotated by motor 16 via container holder 3 for a time period (e.g. 10 seconds) predetermined with a timer.

As shown in FIGS. 8A and 8B, the entire perimeter of holding body 6 of container 5 is split into three. In addition, release slots 8 are present in the thus-split part, and release projections 7 are disposed on the inner peripheral surface of holding body 6. With this configuration, sampling portion 14 of microorganism sampling tool 13 is in a state of being squeezed mostly with release projections 7 (i.e. in a state where release projections 7 are moved while release projections 7 are pushing a long slender strip, in other words, in a state of being subjected to rotary pressure from the outside). This allows an extremely effective release of the microorganisms collected with sampling portion 14, into pure water 10 in holding body 6, and allows a remarkably rapid release of the microorganisms into a wide area of pure water 10 in container 5 via release slots 8.

Note that indicator lamp 18b shown in FIG. 3 flashes during the release of the microorganisms. Moreover, upon expiry of the time period predetermined with the timer described above, the flashing of indicator lamp 18b and the rotation of motor 16 are completed.

When the release operation is completed, sampling portion 14 of microorganism sampling tool 13 is in a state where the lower part and the outer peripheral part thereof are compressed inward as shown in FIG. 7C. In this state, the holding force caused by holding body 6 acts hardly; therefore, the user can easily take out microorganism sampling tool 13 in the upward direction.

Figure 14:
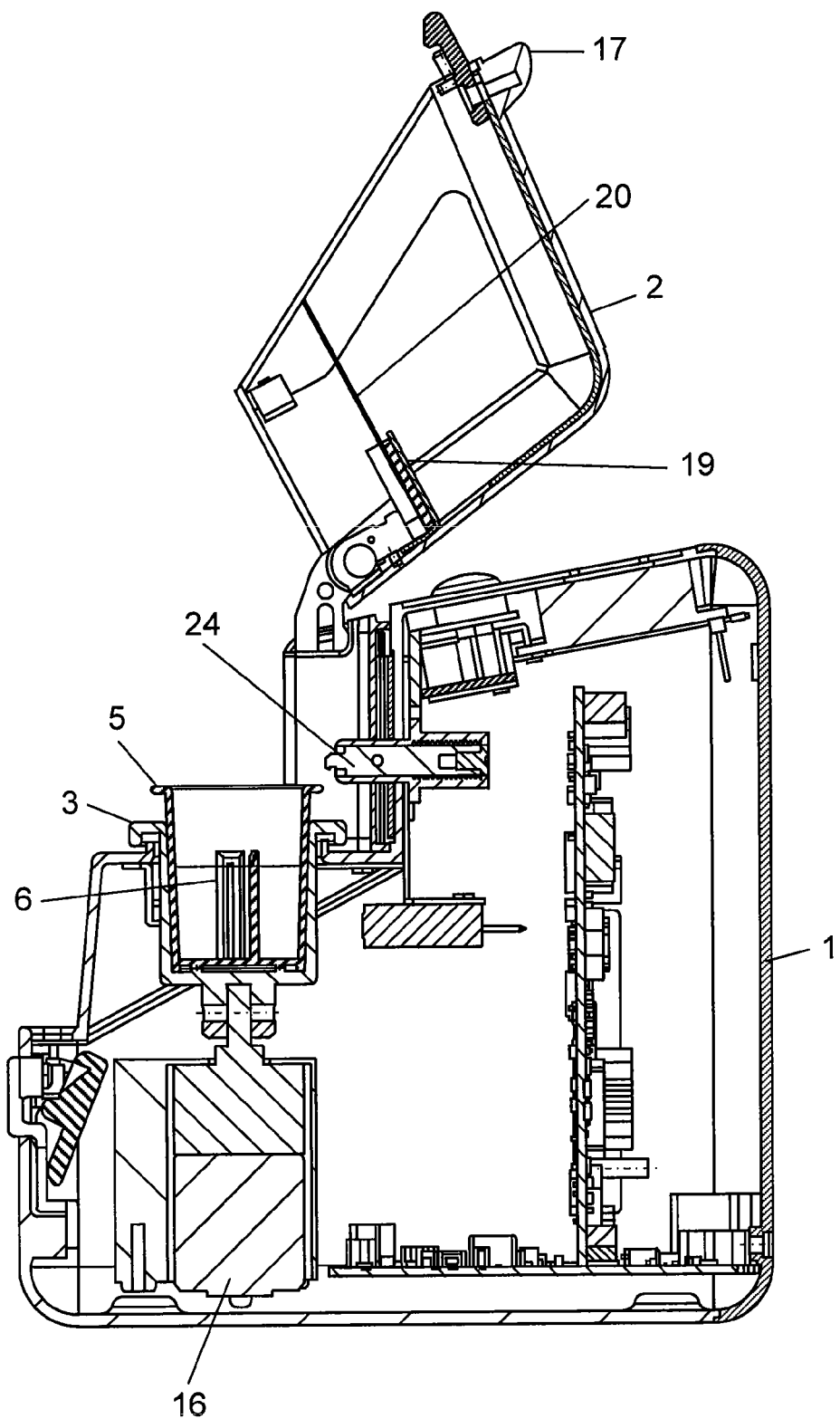
FIG. 14 is a cross-sectional view showing a state where a microorganism sampling tool has been taken out from the container, in the microorganism number-measuring apparatus according to the embodiment of the invention.

FIG. 14 is a cross-sectional view of microorganism number-measuring apparatus 100 according to the embodiment of the invention, in a state where microorganism sampling tool 13 has been taken out from container 5. Moreover, FIG. 15 is a front-elevational view of measurement chip 20 for use in microorganism number-measuring apparatus 100 according to the embodiment of the invention.

Figure 15:
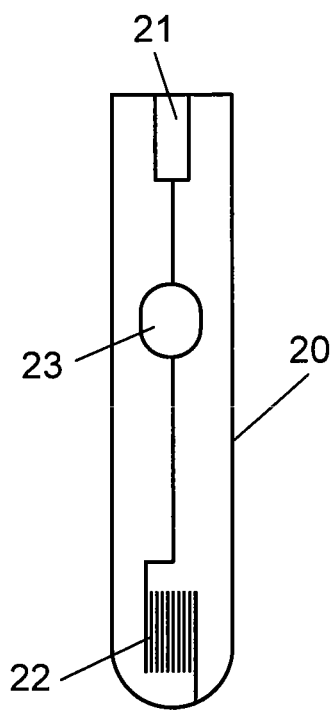
FIG. 15 is a front-elevational view of a measurement chip for use in the microorganism number-measuring apparatus according to the embodiment of the invention.

As shown in FIG. 14, the user sets measurement chip 20 shown in FIG. 15 to measurement-chip holding part 19 that is disposed in the inner surface of front cover 2.

As shown in FIG. 15, measurement chip 20 is a rectangular plate, the lower end of which has a circular arc-shape. Measurement chip 20 is such that the upper end thereof is provided with coupling electrode 21 to be coupled with measurement-chip holding part 19, and the lower end thereof is provided with measurement electrode 22.

The user holds a mid part of measurement chip 20 so as to attach coupling electrode 21 to measurement-chip holding part 19, as shown in FIG. 14. With this configuration, measurement chip 20 is electrically and mechanically coupled with measurement-chip holding part 19.

In microorganism number-measuring apparatus 100 according to the embodiment of the invention, front cover 2 and measurement-chip holding part 19 configure an electrode inserting part. The electrode inserting part causes measurement chip 20 to be inserted into container 5, as described later.

As shown in FIG. 14, in a state where front cover 2 has been lifted and opened, the electrode inserting part is located above container 5, and a measurement-chip-insertion opening of measurement-chip holding part 19 faces upward, toward a direction higher than the horizontal direction.

With this configuration, the user can easily attach coupling electrode 21 of measurement chip 20 to measurement-chip holding part 19, visually ensuring the measurement-chip-insertion opening of measurement-chip holding part 19.

Figure 16:
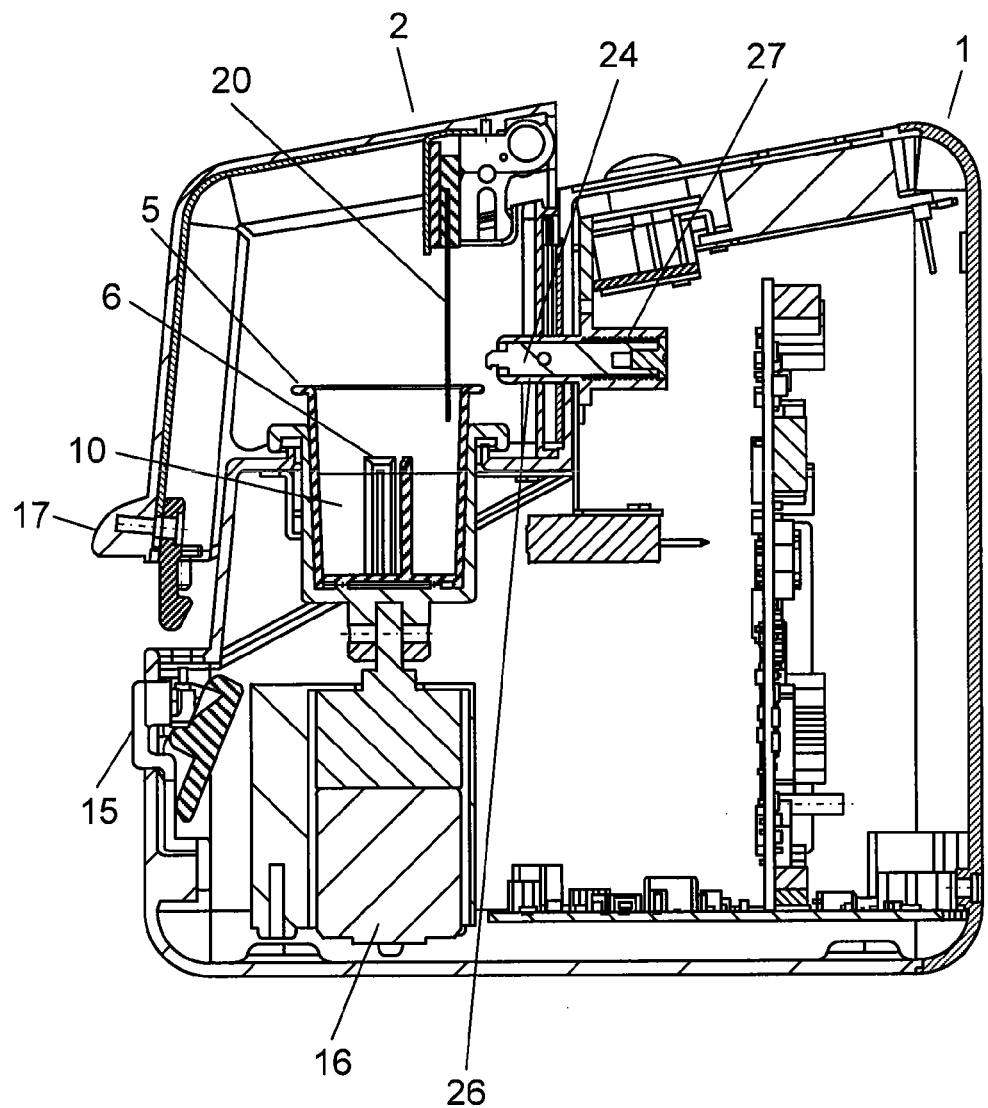
FIG. 16 is a cross-sectional view of the microorganism number-measuring apparatus in operation according to the embodiment of the invention, in the course of closing a front cover thereof.
Figure 17:
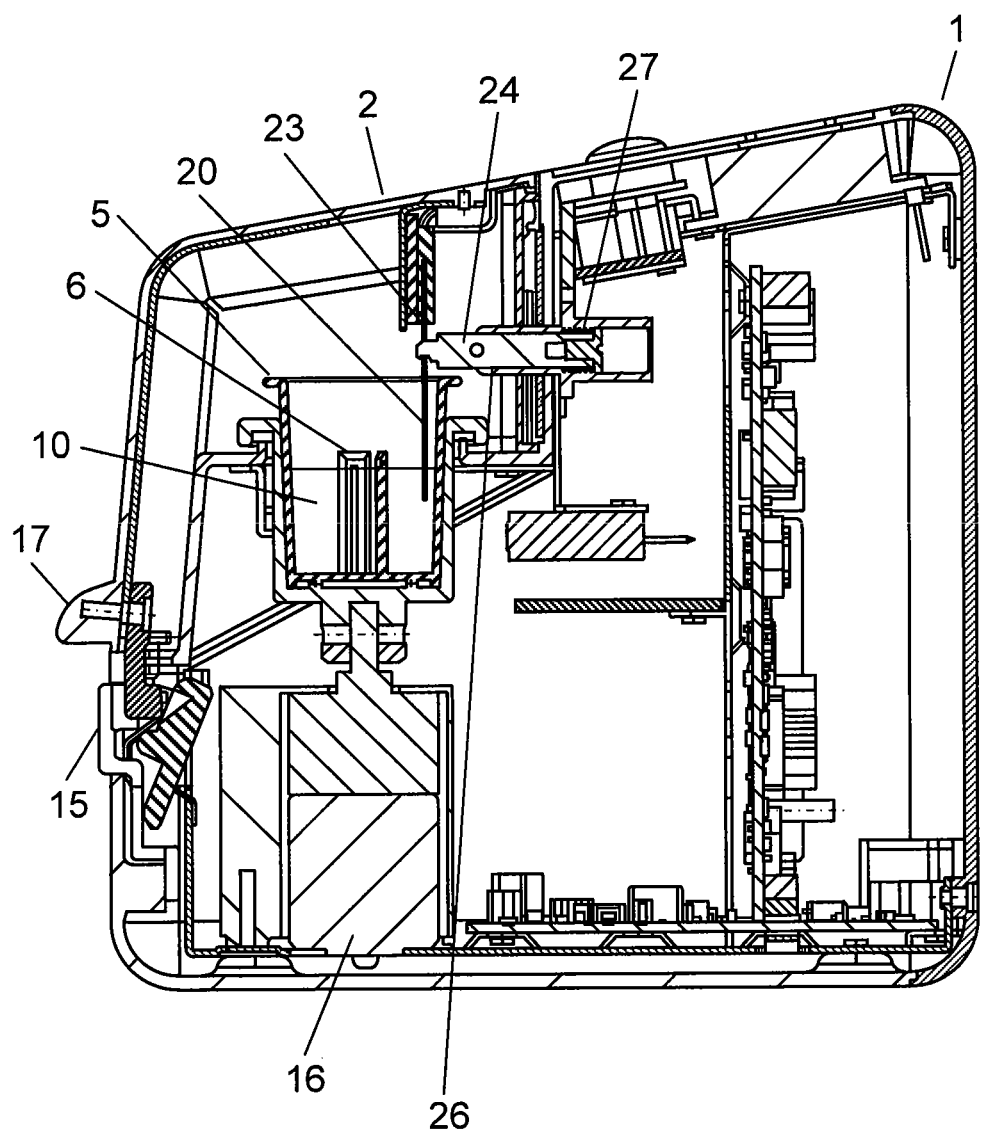
FIG. 17 is a cross-sectional view of the microorganism number-measuring apparatus in operation according to the embodiment of the invention, with the front cover being closed.

FIG. 16 is a cross-sectional view of microorganism number-measuring apparatus 100 in operation according to the embodiment of the invention, in the course of closing the front cover. FIG. 17 is a cross-sectional view of microorganism number-measuring apparatus 100 in operation, with front cover 2 being closed.

Following the state shown in FIG. 14, the user holds handle 17 to rotationally move front cover 2 in the forward and downward direction such that the cover is in a state of covering the front part of body case 1, as shown in FIG. 16. With this operation, measurement chip 20 is in a state of being inserted into the opening in the upper surface of container 5. Starting with this state, additional pushing-down of handle 17 causes front cover 2 to be locked as shown in FIG. 17, with the cover being lowered to the position shown in FIG. 1. At this time, measurement electrode 22 of measurement chip 20 is in a state of being immersed in pure water 10 in container 5.

The user pushes measurement starting switch 36 (FIG. 1), with measurement electrode 22 of measurement chip 20 being immersed in pure water 10 in container 5 by means of the electrode inserting part that includes front cover 2 and measurement-chip holding part 19. Then, measurement electrode 22 is applied with a voltage of e.g. 3 MHz that collects the microorganisms released in container 5, at the measurement electrode 22 part. In addition, concurrently with this, measurement electrode 22 is applied with a voltage of e.g. 800 kHz that measures the number of the microorganisms.

Since the collection of microorganisms and the measurement of the number of the microorganisms are already well known from prior art literatures and the like, their further descriptions are omitted herein. In the embodiment, when measuring the number of the microorganisms, the rotation of container holder 3 and container 5 by motor 16 increases chances with which the microorganisms widely-diffused in container 5 come near measurement electrode 22.

FIG. 17 is a cross-sectional view of microorganism number-measuring apparatus 100 according to the embodiment of the invention, in a state of measuring the number of the microorganisms.

As shown in FIG. 17, in a state where measurement chip 20 is measuring the number of the microorganisms, stick-like operation body 24 configuring a measurement-chip detaching body is inserted into through-hole 23 (FIG. 15) disposed in the mid part of measurement chip 20.

As shown in FIG. 16, operation body 24 is in a state of being retracted backward for a period until the lowering of measurement chip 20 to the inside of container 5 is completed. However, as shown in FIG. 17, operation body 24 moves to protrude in the frontward direction of front cover 2 shortly before the state where the lowering of measurement chip 20 to the inside of container 5 is completed.

Figure 18A:
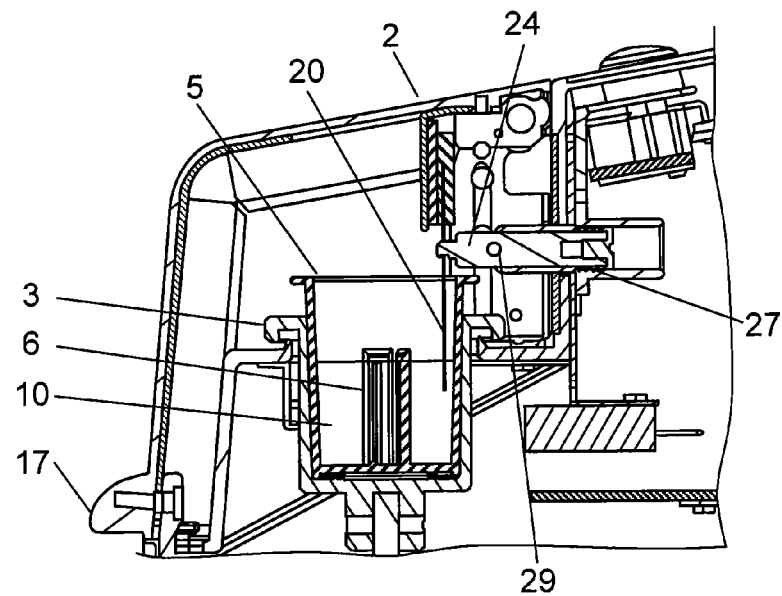
FIG. 18A is a cross-sectional view of a principal part of the microorganism number-measuring apparatus according to the embodiment of the invention, with the front cover being closed.
Figure 18B:
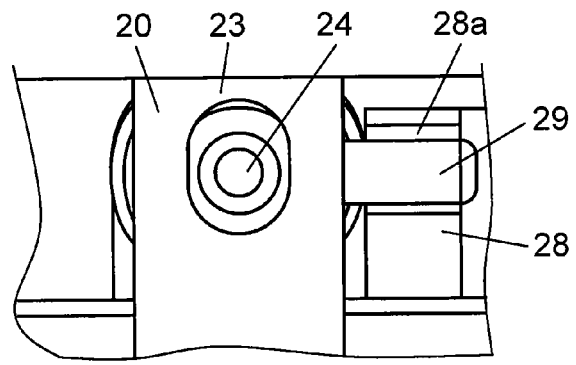
FIG. 18B is a front-elevational view of a part where the measurement chip engages with an operation body, in the microorganism number-measuring apparatus according to the embodiment of the invention.
Figure 18C:
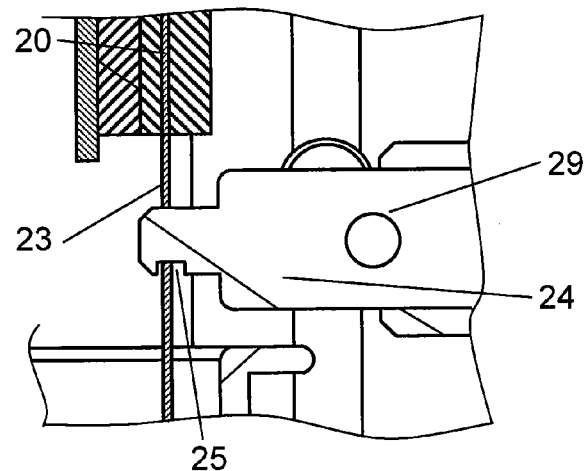
FIG. 18C is a side-elevational view of the part where the measurement chip engages with the operation body, in the microorganism number-measuring apparatus according to the embodiment of the invention.

FIG. 18A is a cross-sectional view of a principal part of microorganism number-measuring apparatus 100 according to the embodiment of the invention, with front cover 2 being closed. FIG. 18B is a front-elevational view of a part of the apparatus where measurement chip 20 engages with operation body 24. FIG. 18C is a side-elevational view of the part.

Through-hole 23 disposed in measurement chip 20 is an elongated hole long in the up-and-down direction, as shown in FIGS. 15 and 18B. Therefore, even before measurement chip 20 is lowered completely, operation body 24 can move to protrude through through-hole 23.

Moreover, as shown in FIG. 18C, hook-like engagement part 25 is disposed at the lower surface of the tip of operation body 24 such that engagement part 25 can engage with the lower-end side of through-hole 23 of measurement chip 20, when detaching measurement chip 20 as described later.

In the embodiment, the measurement of the number of the microorganisms is performed in the state shown in FIG. 17. After the measurement, when the user widely opens front cover 2 so as to take out measurement chip 20, measurement chip 20 is greatly lifted together with front cover 2 to the outside of container 5. At this time, measurement chip 20 is already in a state where the measurement has been performed in container 5.

When measurement chip 20 after the measurement is greatly lifted upward together with front cover 2 in this way, pure water 10 that contains the microorganisms will possibly accidentally splatter or drop in the forward and downward direction of front cover 2, with the water having adhered to the measurement chip during the measurement. As countermeasures against this, in the embodiment, operation body 24 is disposed to configure the measurement-chip detaching body as described above.

More specific details of this point will be described here. The state of measurement chip 20 being measuring the number of the microorganisms is, that is, one where measurement electrode 22 of measurement chip 20 is immersed in pure water 10, as shown in FIG. 17. At this time, operation body 24 is in a state of having moved to protrude through through-hole 23 of measurement chip 20.

In this way, it is the mechanism shown in FIGS. 11 and 12 that causes operation body 24 to move to protrude, from the state shown in FIG. 16 to the state shown in FIG. 17, and that causes the operation body to move to retract, from the state shown in FIG. 17 to the state shown in FIG. 16.

Operation body 24 is slidably disposed in the inside of cylinder-shaped guide tube 26. Guide tube 26 is secured to body case 1. Moreover, in the state of front cover 2 being opened as shown in FIGS. 12 and 16, operation body 24 is in a state of always being biased, by spring 27 (FIG. 16), against the opposite side (the right side of FIG. 16) of front cover 2, in the inside of guide tube 26.

Descriptions will be made here regarding the operation in which front cover 2 is further pushed downward, from the state shown in FIG. 16 to the state shown in FIG. 17, such that measurement electrode 22 of measurement chip 20 is immersed in pure water 10. At this time, interlocking with the downward movement of front cover 2, cam plate 28 moves downward, from the state shown in FIG. 12 to the state shown in FIG. 11. With this configuration, operation body 24 can be moved to protrude toward measurement chip 20.

That is, cam plate 28 has the configuration in which the upper part thereof more largely protrudes toward front cover 2 (toward measurement chip 20) than the lower part thereof. Therefore, as cam plate 28 is lowered, the upper part of the cam plate pushes operation pin 29 of operation body 24 toward front cover 2 (toward measurement chip 20). As a result, operation body 24 moves to enter through-hole 23 of measurement chip 20, as shown in FIGS. 18A to 18C.

When operation body 24 moves to protrude toward front cover 2 (toward measurement chip 20) in this way, spring 27 is in a state of being compressed as shown in FIGS. 17 and 18A.

Figure 19A:
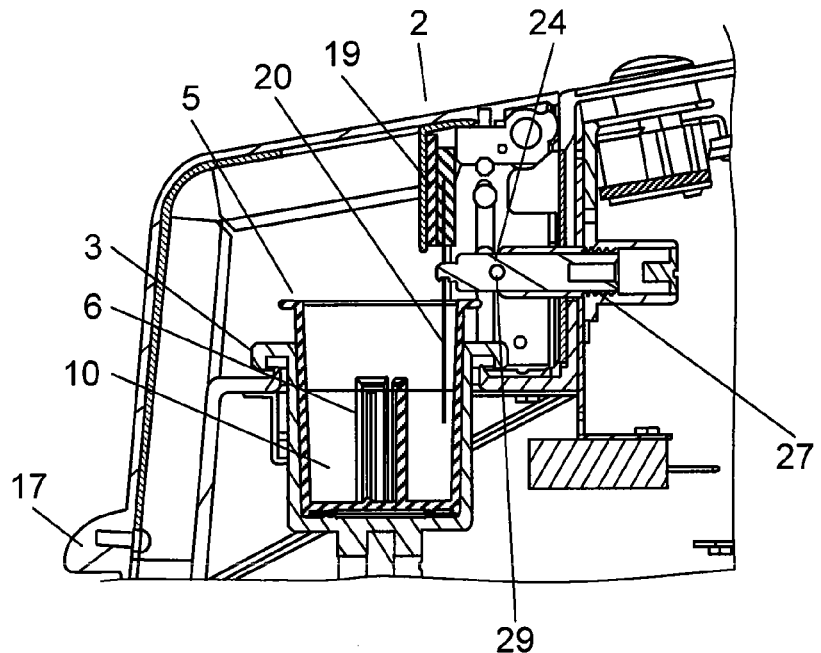
FIG. 19A is a cross-sectional view of the principal part of the microorganism number-measuring apparatus according to the embodiment of the invention, which shows a state immediately after the front cover starts to be lifted by a return force of springs, after measurement of the number of microorganisms.
Figure 19B:
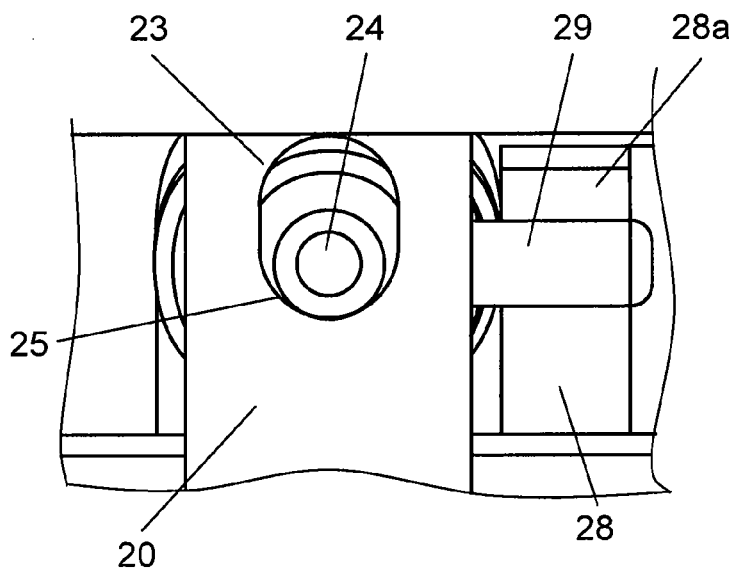
FIG. 19B is a front-elevational view of the part where the measurement chip engages with the operation body, which shows the state immediately after the front cover starts to be lifted by the return force of the springs, after the measurement of the number of the microorganisms, in the microorganism number-measuring apparatus according to the embodiment of the invention.

FIG. 19A is a cross-sectional view of a principal part of microorganism number-measuring apparatus 100 according to the embodiment of the invention, which shows a state immediately after front cover 2 starts to be lifted by the return force of springs 16a, after the measurement of the number of microorganisms. FIG. 19B is a front-elevational view of a part where measurement chip 20 engages with operation body 24.

At this time, since protruded plane 28a (FIG. 19B) is formed at the upper end of cam plate 28, operation body 24 does not retract but remains in place (FIG. 19A), in the state immediately after front cover 2 starts to be lifted.

However, measurement chip 20 is in a state where coupling electrode 21 of the upper end of the chip is held by measurement-chip holding part 19. Measurement chip 20 is slightly lifted as front cover 2 moves slightly upward, as shown in 19A. As a result, hook-like engagement part 25 of operation body 24 engages with the lower end of through-hole 23 of measurement chip 20, as shown in FIG. 19B.

Figure 20A:
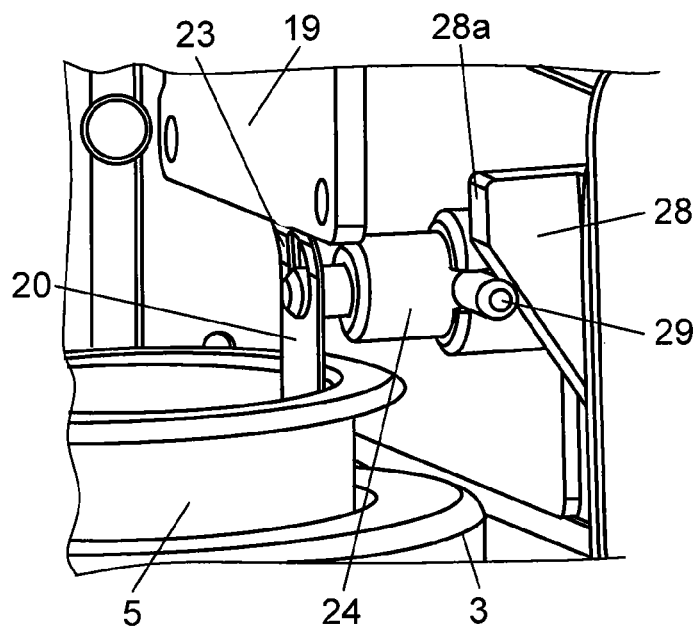
FIG. 20A is a perspective view of a principal part of the microorganism number-measuring apparatus according to the embodiment of the invention, which shows a state where the front cover has been further lifted, from the previous state shown in FIGS. 19A and 19B.
Figure 20B:
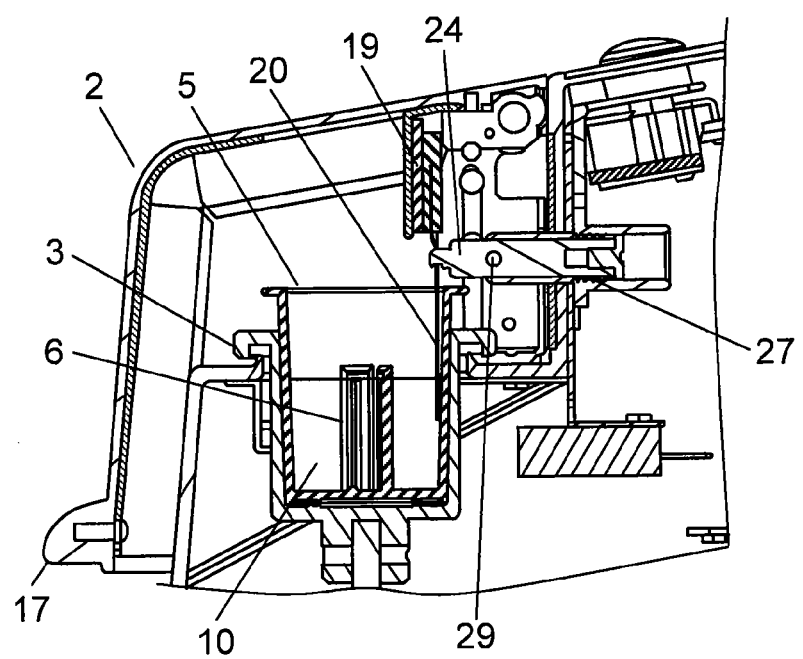
FIG. 20B is a cross-sectional view of the principal part of the microorganism number-measuring apparatus according to the embodiment of the invention, which shows the state where the front cover has been further lifted, from the previous state shown in FIGS. 19A and 19B.

FIG. 20A is a perspective view of a principal part of microorganism number-measuring apparatus 100 according to the embodiment of the invention, which shows a state where front cover 2 is further lifted, from the previous state shown in FIGS. 19A and 19B. FIG. 20B is a cross-sectional view of the principal part.

As shown in FIGS. 20A and 20B, the further lifting of front cover 2 causes operation pin 29 of operation body 24 to move away from plane 28a of cam plate 28, and to move to an inclining part of cam plate 28.

As a result, operation body 24 retracts backward by a return force of spring 27. With this configuration, a part lower than through-hole 23 of measurement chip 20 that has flexibility is forced to move backward, and, after a while, becomes in a state where the part is pressed against the inner wall surface of container 5, as shown in FIG. 20B.

Note that, as described above, hook-like engagement part 25 is disposed at the tip of operation body 24; therefore, the part lower than through-hole 23 of measurement chip 20 can be pulled backward with stability.

On the other hand, since a part upper than through-hole 23 of measurement chip 20 is held by measurement-chip holding part 19, the upper part becomes in a state of being inclined frontward more than the lower part.

Figure 21:
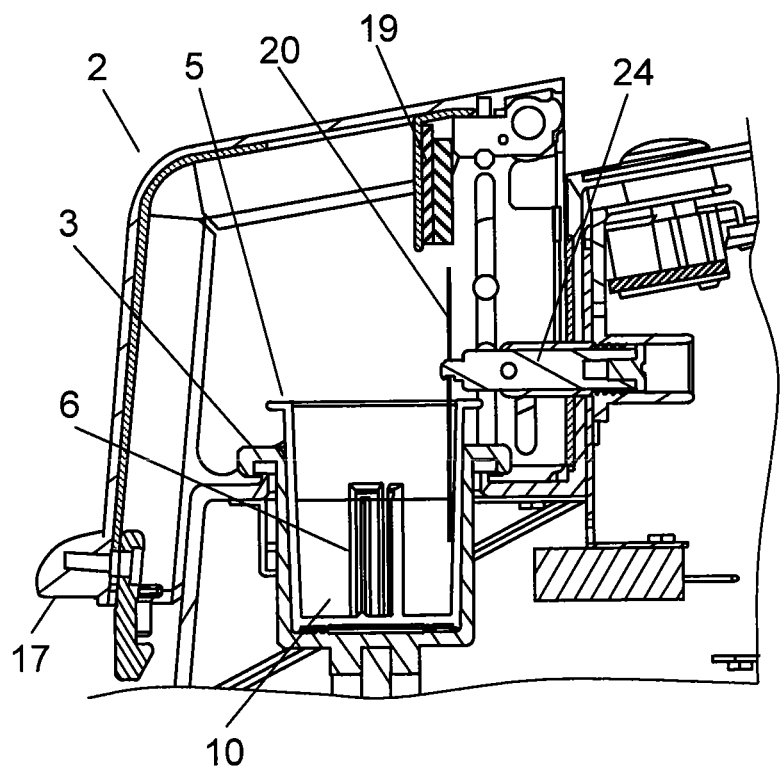
FIG. 21 is a cross-sectional view of the principal part of the microorganism number-measuring apparatus according to the embodiment of the invention, which shows a state where the front cover has been still further lifted, from the previous state shown in FIGS. 20A and 20B.

FIG. 21 is a cross-sectional view of the principal part of microorganism number-measuring apparatus 100 according to the embodiment of the invention, which shows a state where front cover 2 is still further lifted, from the previous state shown in FIGS. 20A and 20B.

When front cover 2 is lifted to the state shown in FIG. 21, coupling electrode 21 of measurement chip 20 is detached from measurement-chip holding part 19. In this state, the user lifts and opens front cover 2 to the position shown in FIG. 14 by means of handle 17, and then takes out measurement chip 20 from container 5.

In this way, in the embodiment, it is configured that, even when front cover 2 is lifted and opened, measurement chip 20 is not lifted to the outside of container 5 in interlock with the lift-and-open operation of the cover.

For this reason, the lift-and-open operation of front cover 2 does not cause microorganism-containing pure water 10 to accidentally splatter or drop in the forward and downward direction of front cover 2, with the water having adhered to the measurement chip during the measurement. This is preferable in view of hygiene.

In the embodiment, in order to take out measurement chip 20 that is in the state of being held by operation body 24 as shown in FIG. 21, a coupling electrode 21 part of the upper end of measurement chip 20 is held and pushed down slightly toward the inside of container 5 located below. With this operation, engagement part 25 of operation body 24 is disengaged from through-hole 23, which allows the user to easily take out measurement chip 20 to the outside of container 5.

Moreover, since the coupling electrode 21 part of the upper end for use in taking out measurement chip 20 is a part that has not been immersed in pure water 10 in container 5, the holding of the part does not cause any problem in view of hygiene.

Figure 22A:
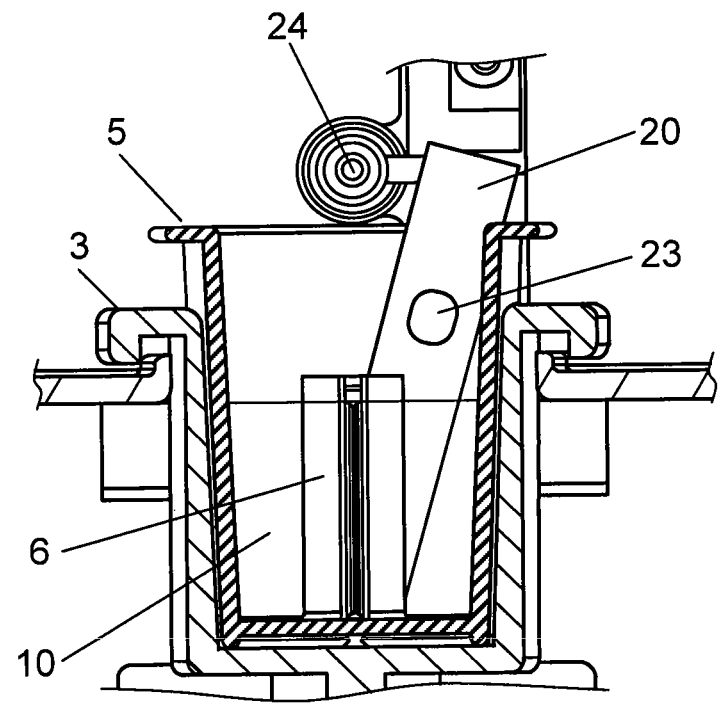
FIG. 22A is a cross-sectional view of a principal part of the microorganism number-measuring apparatus according to the embodiment of the invention, which shows a state where the measurement chip has been erroneously dropped during operation of taking out the measurement chip.
Figure 22B:
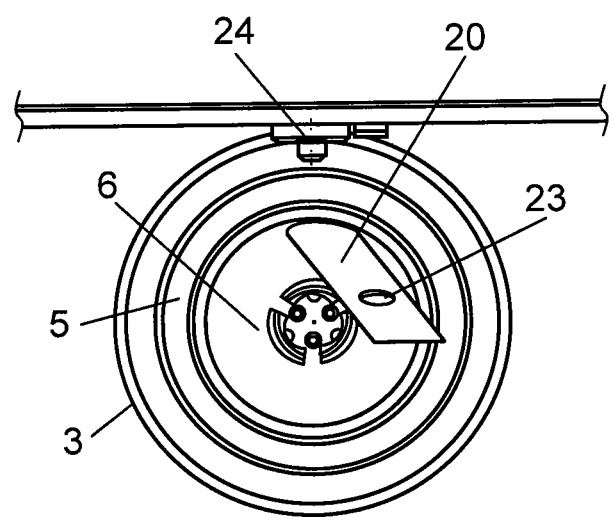
FIG. 22B is a plan view of the principal part of the microorganism number-measuring apparatus according to the embodiment of the invention, which shows the state where the measurement chip has been erroneously dropped during the operation of taking out the measurement chip.

FIG. 22A is a cross-sectional view of a principal part of microorganism number-measuring apparatus 100 according to the embodiment of the invention, which shows a state where measurement chip 20 has been erroneously dropped during the operation of taking out measurement chip 20. FIG. 22B is a plan view of the principal part.

As shown in FIGS. 22A and 22B, thus-dropped measurement chip 20 is held in container 5. This configuration prevents measurement chip 20 from accidentally being dropped onto the floor or the like, which also does not cause a problem in view of hygiene.

Moreover, in the embodiment, the length of measurement chip 20 is configured larger than the depth of container 5. With this configuration, if measurement chip 20 should be dropped into container 5 as shown in FIGS. 22A and 22B, the user can hold the upper end of measurement chip 20 without touching pure water 10 in container 5. This allows the user to easily take out measurement chip 20 and to dispose of it.

Figure 23:
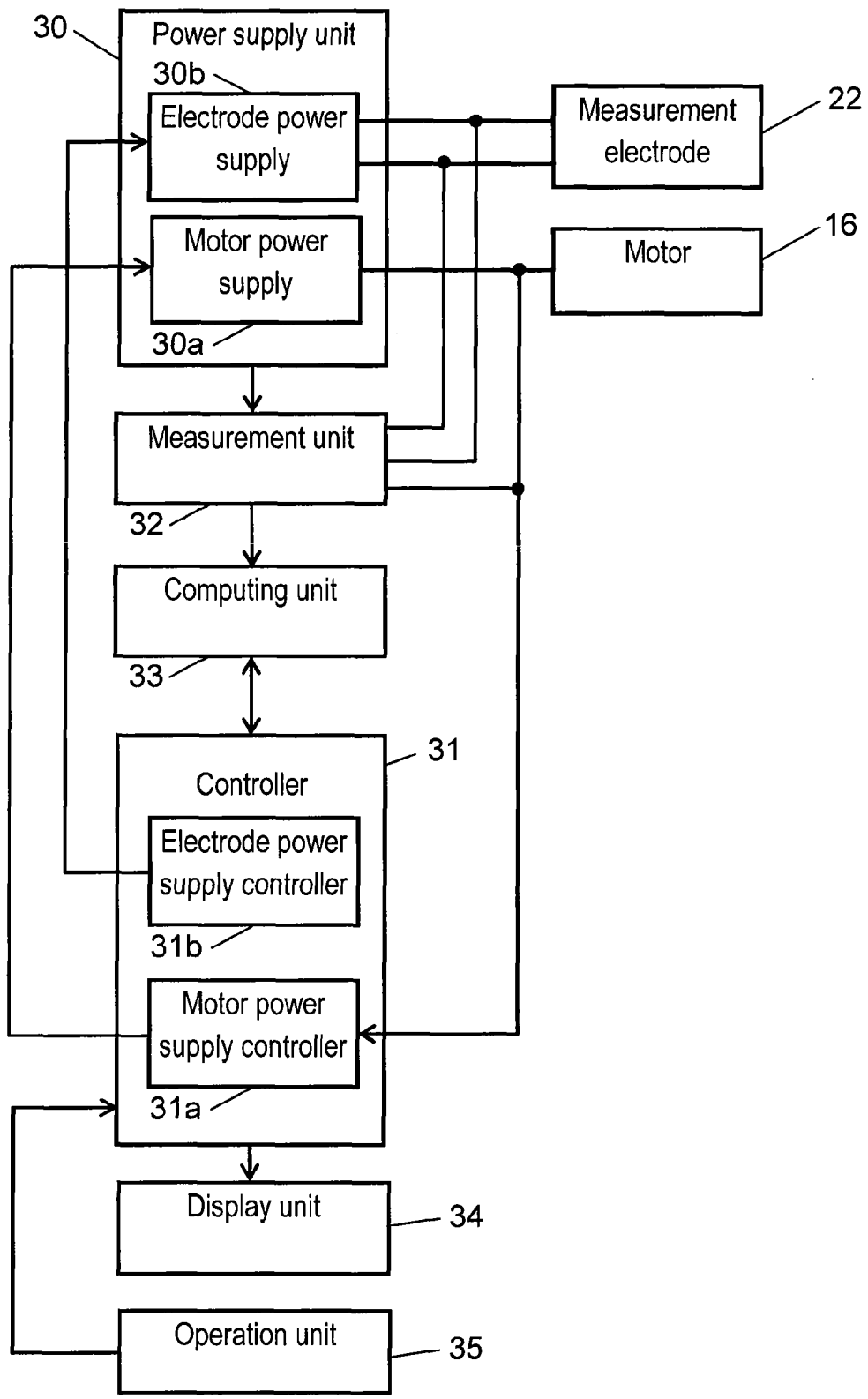
FIG. 23 is a control block diagram of the microorganism number-measuring apparatus according to the embodiment of the invention.

FIG. 23 is a control block diagram of microorganism number-measuring apparatus 100 according to the embodiment of the invention.

Microorganism number-measuring apparatus 100 includes measurement electrode 22, motor 16, power supply unit 30, measurement unit 32, computing unit 33, controller 31, display unit 34, and operation unit 35.

Power supply unit 30 includes electrode power supply 30b and motor power supply 30a. Controller 31 includes electrode-power-supply controller 31b and motor-power-supply controller 31a.

Measurement electrode 22 is coupled with electrode power supply 30b and measurement unit 32.

Motor 16 is coupled with motor power supply 30a of power supply unit 30, measurement unit 32, and motor-power-supply controller 31a.

Electrode power supply 30b is coupled with measurement unit 32 and electrode-power-supply controller 31b.

Motor power supply 30a is coupled with motor-power-supply controller 31a of controller 31.

Power supply unit 30 is coupled with measurement unit 32.

Measurement unit 32 is coupled with computing unit 33 and motor-power-supply controller 31a.

Computing unit 33 is coupled with controller 31.

Controller 31 is coupled with display unit 34.

Electrode power supply 30b applies above-described voltages of 3 MHz and 800 kHz to measurement electrode 22. Simultaneously with this, the number of the microorganisms is measured by means of computing unit 33 and measurement unit 32 coupled with measurement electrode 22. The measured value is displayed on display unit 34 disposed in a rearward position of front cover 2.

Note that, in FIG. 23, operation unit 35 coupled with controller 31 is one for operating the power supplies. Moreover, although not shown in FIG. 23, switch 18a, indicator lamp 18b, measurement starting switch 36, and the like shown in FIG. 3 are each coupled with controller 31.

Figure 24:
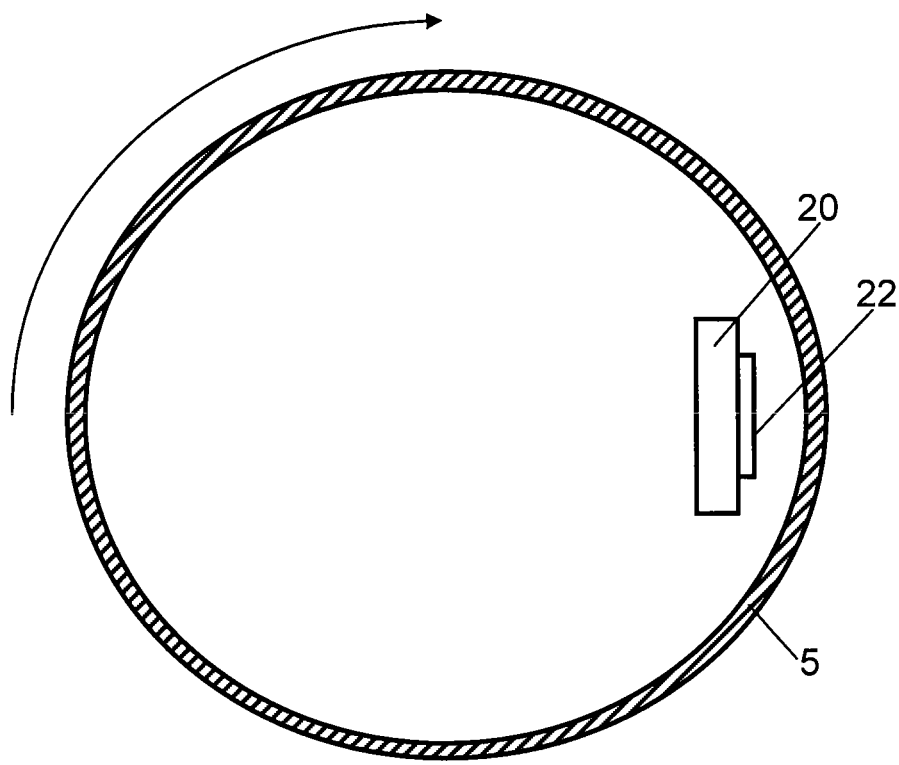
FIG. 24 is a top view of a principal part of the microorganism number-measuring apparatus according to the embodiment of the invention, for illustrating functions of the apparatus.
Figure 25:
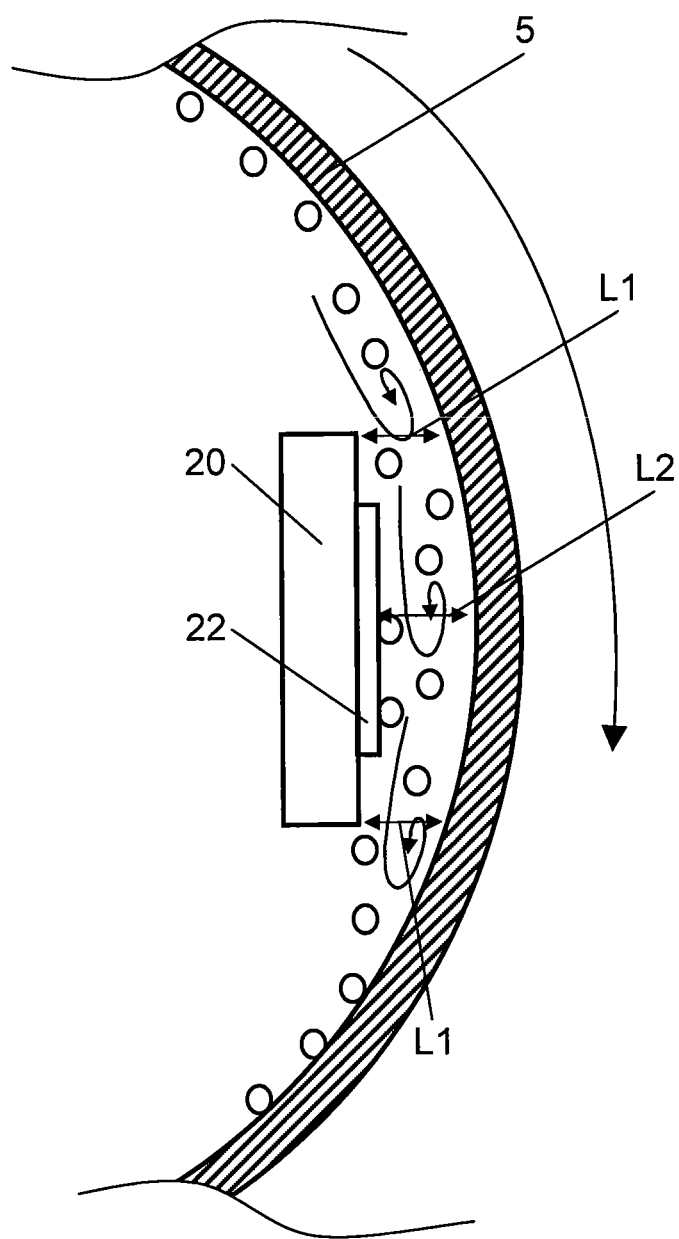
FIG. 25 is a top view of a principal part of the microorganism number-measuring apparatus according to the embodiment of the invention, for illustrating the functions of the apparatus.

FIGS. 24 and 25 are each a top view of a principal part of microorganism number-measuring apparatus 100 according to the embodiment of the invention, for illustrating functions of the apparatus. Incidentally, FIG. 25 is an enlarged view of the part indicated by dashed lines of FIG. 28 to be described later.

Measurement chip 20 of the embodiment is a rectangular plate as shown in FIG. 15, the upper end of which is provided with coupling electrode 21 to be coupled with measurement-chip holding part 19, and the lower part of which is provided with measurement electrode 22.

Accordingly, the electric and mechanical coupling can be obtained by holding the mid part of measurement chip 20 and by attaching measurement electrode 21 to measurement-chip holding part 19 as shown in FIG. 14.

Measurement chip 20 held by measurement-chip holding part 19 becomes in a state of being immersed in pure water 10 in container 5, as shown in FIG. 17.

At this time, as shown in FIG. 24, measurement chip 20 is disposed at the position that is closer to the inner surface of container 5 than to the center axis of container 5 and is away from the inner surface of container 5 with a predetermined distance. Moreover, in this state, measurement electrode 22 of measurement chip 20 is disposed to face the inner surface of container 5.

As a result, measurement chip 20 having a rectangular plate shape, the lower end of which is provided with measurement electrode 22, is disposed as follows: In a horizontal cross-section, as shown in FIG. 25, distance (L1) is smaller than distance (L2) where distance (L1) is from each of the left and right ends of measurement chip 20 to the respectively-facing inner surface of container 5, and distance (L2) is from the center part between the left and right ends of measurement chip 20 to the corresponding inner surface of container 5.

In this state, when measuring the number of the microorganisms, container 5 is rotated by motor 16 (an example of a rotary driver) via container holder 3.

Figure 26:
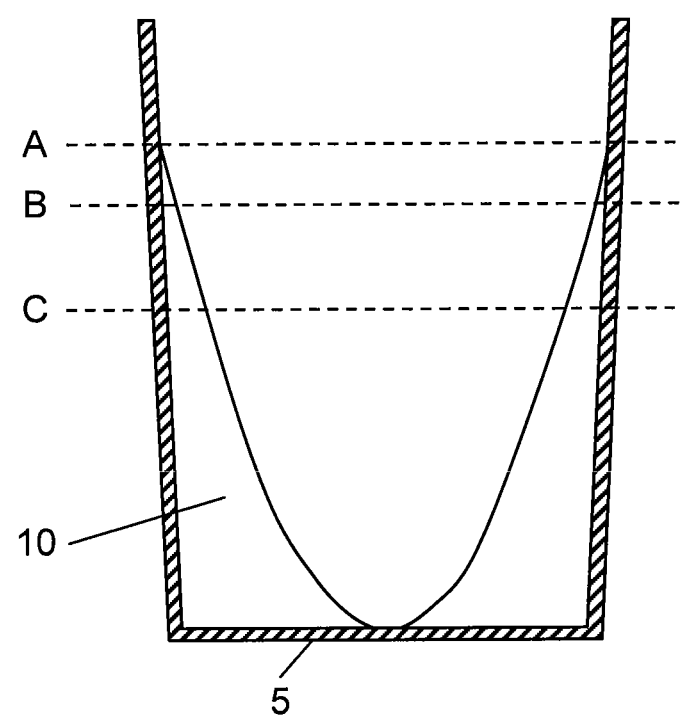
FIG. 26 is a cross-sectional view of a principal part of the microorganism number-measuring apparatus according to the embodiment of the invention, for illustrating the functions of the apparatus.
Figure 27:
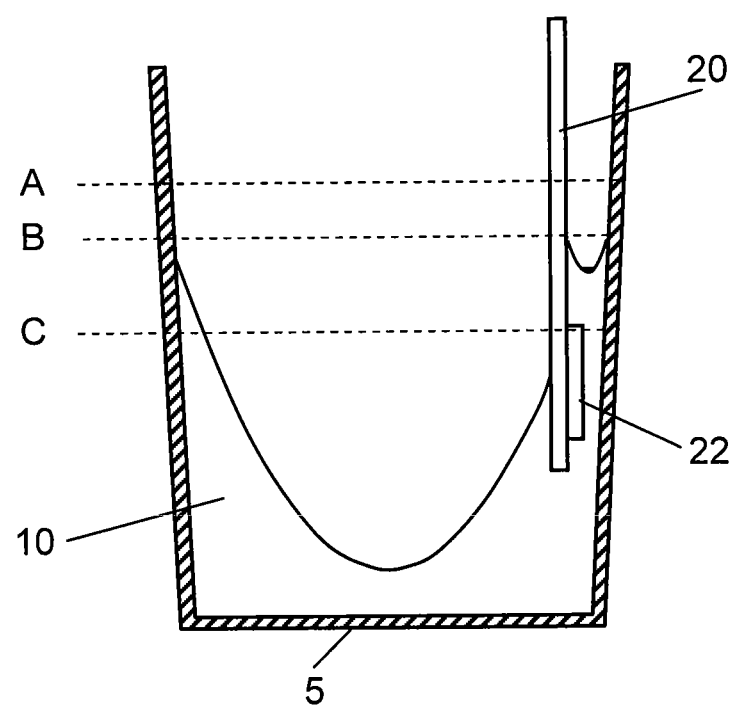
FIG. 27 is a cross-sectional view of a principal part of the microorganism number-measuring apparatus according to the embodiment of the invention, for illustrating the functions of the apparatus.

FIGS. 26 and 27 are each a cross-sectional view of a principal part of microorganism number-measuring apparatus 100 according to the embodiment of the invention, for illustrating the functions of the apparatus.

As shown in FIG. 26, pure water 10 turns about the center axis in the up-and-down direction, which causes a whirlpool state. For easy understanding of this point, the case is shown in FIG. 26 where measurement chip 20 and holding body 6 are absent. Assume that the liquid level of pure water 10 is at position "C" when container 5 is not in rotation. When container 5 rotates, the rotary-axis part of pure water 10 is largely recessed, and, in contrast, the outer peripheral part (the part at the inner surface of container 5) of the water is raised up to position "A." That is, a whirlpool-shaped turning flow is formed in container 5.

On the other hand, the case is shown in FIG. 27 where measurement chip 20 described above is disposed in container 5 (but, for avoiding complexity in description, holding body 6 is assumed to be absent).

As shown in FIG. 27, the aforementioned whirlpool-shaped turning flow undergoes resistance caused by the presence of measurement chip 20, which causes the outer peripheral part to be raised only up to position "B" that is located lower than position "A" described above.

However, in the embodiment, measurement chip 20 is disposed in proximity of the inner surface of container 5, as shown in FIG. 27. With this configuration, a rising part of pure water 10 is formed by surface tension at a portion surrounded by measurement chip 20 and the inner surface of container 5. As a result, as clearly shown in FIG. 27, measurement electrode 22 becomes in a state of being reliably immersed in pure water 10.

Figure 28:
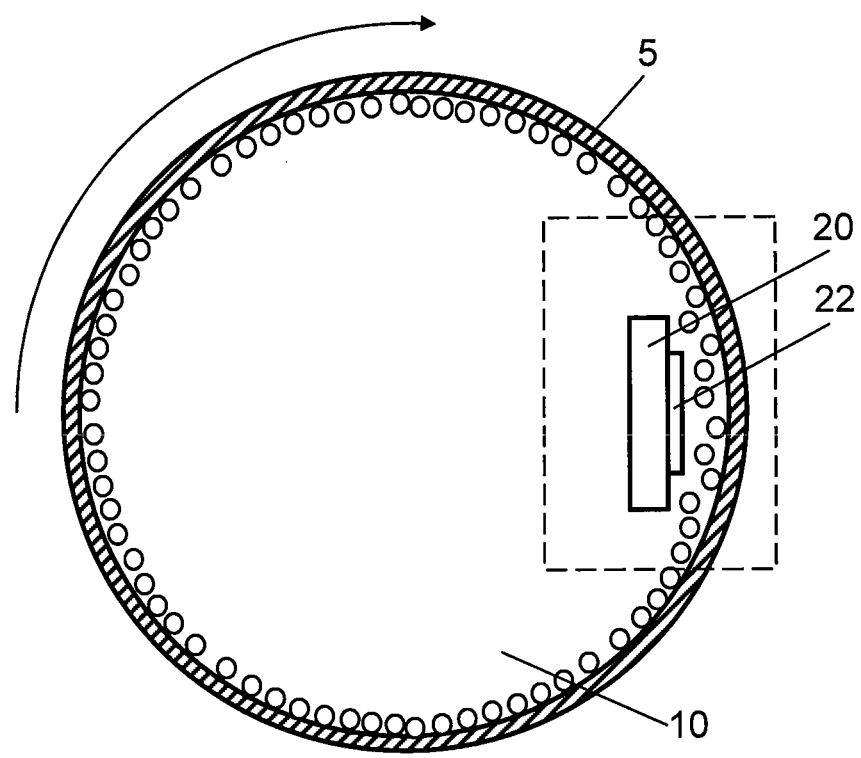
FIG. 28 is a schematic plan view of a principal part of the microorganism number-measuring apparatus according to the embodiment of the invention, which shows a state where the microorganisms in pure water are biased against the inner surface of the container by a centrifugal force caused by a turning flow in the container.

FIG. 28 is a schematic plan view of a principal part of microorganism number-measuring apparatus 100 according to the embodiment of the invention, which shows a state where the microorganisms in pure water 10 are biased against the inner surface of container 5 by a centrifugal force caused by the turning flow in container 5.

As shown in FIG. 28, the microorganisms are turned by the turning flow, with the microorganisms being biased against the inner surface of container 5.

With this configuration, in the embodiment, as described above, measurement chip 20 is of a rectangular plate shape, and is disposed as follows: In a horizontal cross-section, distance (L1 in FIG. 25) is smaller than distance (L2 in FIG. 25) where distance L1 is from each of the left and right ends of measurement chip 20 to the respectively-facing inner surface of container 5, and distance L2 is from the center portion between the left and right ends of measurement chip 20 to the corresponding inner surface of container 5.

With this configuration, as shown in FIG. 25, the turning flow passes the portion of L1, and then causes a turbulence phenomenon where the flow passes the portion of L2 that is longer than L1. As a result, as shown in FIG. 25, being biased against the inner surface of container 5, the microorganisms that flow along the inner surface are conducted toward measurement electrode 22 as well, which allows the microorganisms to be collected by measurement electrode 22.

That is, the turbulence can actively conduct, to measurement electrode 22, the microorganisms that are being biased against the inner surface of container 5 and are flowing along the surface.

As a result, use of microorganism number-measuring apparatus 100 according to the embodiment allows the effective collection of the microorganisms, resulting in increased measurement accuracy.

Moreover, in microorganism number-measuring apparatus 100 according to the embodiment, the electrode inserting part is disposed for inserting measurement chip 20 into container 5 from above container 5 held container holder 3, via the container's opening. Accordingly, container 5 may be of a simple blind-cylinder shape that has the opening in the upper surface thereof, which allows a reduced cost of manufacturing container 5, resulting in a reduced cost of the measurement.

INDUSTRIAL APPLICABILITY

As described above, according to the present invention, it is possible to present the microorganism number-measuring apparatus that is capable of reducing measurement costs and increasing measurement accuracy. Therefore, the present invention is useful for a microorganism number-measuring apparatus that measures the number of microorganisms or the like, present inside an oral cavity or in food.

REFERENCE MARKS IN THE DRAWINGS 1 body case
2 front cover
3 container holder
4 drive projection
5 container
6 holding body
7 release projection
8 release slot
9 release projection
10 pure water
11 lid
12 projection
13 microorganism sampling tool
14 sampling portion
15 operation button
16a spring
16 motor
17 handle
18a switch
18b indicator lamp
19 measurement-chip holding part
20 measurement chip
21 coupling electrode
22 measurement electrode
23 through-hole
24 operation body
25 engagement part
26 guide tube
27 spring
28 cam plate
28a plane
29 operation pin
30 power supply unit
30a motor power supply
30b electrode power supply
31 controller
31a motor-power-supply controller
31b electrode-power-supply controller
32 measurement unit
33 computing unit
34 display unit
36 operation unit
36 measurement starting switch
100 microorganism number-measuring apparatus

The invention claimed is:

1. A microorganism number-measuring apparatus, comprising:
a container holder for holding a container having a cylinder shape and an opening in an upper surface of the container, the opening being positioned upward;
a rotary driver for rotating the container holder configured to hold the container, about a rotary axis in an up-and-down direction;
an electrode inserting part for moving a measurement chip being of a rectangular plate shape through the opening of the container from a position above the container while the container is held by the container holder, and for holding the measurement chip closer to a container's inner surface than to a container's center axis without touching the container's inner surface; and
a measurement unit for measuring microorganisms by using a measurement electrode of the measurement chip inserted into the container by the electrode inserting part;
wherein
the electrode inserting part holds the measurement chip being of the rectangular plate shape in a state of a surface on which the measurement electrode is provided facing the container's inner surface.

2. The microorganism number-measuring apparatus according to claim 1,
wherein
the measurement chip is provided with the measurement electrode at an lower end of the chip, and,
in a horizontal cross-section, a distance from each of left and right ends of the measurement chip to the container's inner surface facing the respective ends is smaller than a distance from a center portion between the left and right ends to the container's inner surface facing the center portion.

3. The microorganism number-measuring apparatus according to claim 2,
wherein the rotary driver rotating the container held by the container holder about the rotary axis in the up-and-down direction makes a liquid accommodated in the container a turbulence state between the inner surface of the container and the measurement chip being of the rectangular plate shape, and
the measurement unit measures microorganisms in the turbulence state.

4. The microorganism number-measuring apparatus according to claim 1,
wherein the rotary driver rotates the container in a state holding an outer surface of the container.

5. The microorganism number-measuring apparatus according to claim 4,
wherein the container holder has a blind-cylinder shape and an opening in an upper surface of the container holder.

6. The microorganism number-measuring apparatus according to claim 5,
wherein the container holder has a drive protection protruding in a direction toward an engaging part provided on an outer surface of a bottom of the container.

* * * * *